United States Patent [19]

Samain

[11] Patent Number: 5,769,902

[45] Date of Patent: Jun. 23, 1998

[54] COMPSITIONS FOR DYEING KERATINOUS FIBERS COMPRISING AN ORTHO-DIAMINOPYRAZOLES, A COUPLER OR DIRECT DYE, AND A MANGANESE SALT, AND PROCESSES FOR DYEING KERATINOUS FIBERS WITH THESE COMPOSITIONS

[75] Inventor: Henri Samain, Bievres, France

[73] Assignee: L'Oreal, Paris, France

[21] Appl. No.: 666,824

[22] Filed: Jun. 19, 1996

[30] Foreign Application Priority Data

Jun. 21, 1995 [FR] France .................................. 95 07433

[51] Int. Cl.⁶ ..................................................... A61K 7/13
[52] U.S. Cl. ......................... 8/409; 8/407; 8/408; 8/423; 8/628
[58] Field of Search ............................... 8/405, 406, 408, 8/409, 423, 429, 407, 628

[56] References Cited

U.S. PATENT DOCUMENTS

| | | | |
|---|---|---|---|
| 3,838,966 | 10/1974 | Barchas et al. ............................. | 8/405 |
| 4,776,856 | 10/1988 | Tennigkeit et al. ......................... | 8/406 |
| 5,061,289 | 10/1991 | Clausen et al. ............................. | 8/405 |
| 5,199,954 | 4/1993 | Schultz et al. .............................. | 8/408 |
| 5,368,610 | 11/1994 | Chan et al. ................................. | 8/408 |
| 5,534,267 | 7/1996 | Neunhoeffer et al. ...................... | 8/409 |

FOREIGN PATENT DOCUMENTS

| | | |
|---|---|---|
| A-375977 | 7/1990 | European Pat. Off. . |
| A-2090272 | 1/1972 | France . |
| A-4234887 | 4/1994 | Germany . |

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

Compositions for dyeing keratinous fibers comprising at least one an ortho-diaminopyrazole or an acid addition salt thereof and a manganese salt as well as a dyeing process using these compositions, without any oxidizing agent other than atmospheric oxygen.

30 Claims, No Drawings

COMPSITIONS FOR DYEING KERATINOUS FIBERS COMPRISING AN ORTHO-DIAMINOPYRAZOLES, A COUPLER OR DIRECT DYE, AND A MANGANESE SALT, AND PROCESSES FOR DYEING KERATINOUS FIBERS WITH THESE COMPOSITIONS

The present invention is directed to new compositions for dyeing keratinous fibers, in particular human keratinous fibers such as hair, comprising, in the form of a mixture or separately, at least one ortho-diaminopyrazole and at least one manganese salt, as well as to a dyeing process using these compositions, the color being developed without any oxidizing agent other than atmospheric oxygen.

It is known to dye keratinous fibers, in particular human hair, with dyeing compositions containing appropriate oxidation dye precursors, in particular ortho- or para-phenylenediamines, ortho- or para-aminophenols, and heterocyclic compounds such as diaminopyrazole derivatives, which are generally called oxidation bases. The oxidation dye precursors, or oxidation bases, are colorless or weakly colored compounds which, when combined with suitable oxidizing agents, can give rise, by a process of oxidative condensation, to colored and coloring compounds.

It is also known that the shades obtained with these oxidation bases can be varied by combining them with couplers or color modifiers, the latter being chosen particularly from aromatic meta-diamines, meta-aminophenols, meta-diphenols and certain heterocyclic compounds.

The variety of molecules used as oxidation bases and couplers allow a rich palette of colors to be obtained.

The so-called "permanent" color obtained by virtue of these oxidation dyes should, moreover, meet a number of requirements; it should have no drawback from the toxicological point of view, it should make it possible to obtain shades of desired intensity and should exhibit good behavior in relation to external agents, such as light, adverse weather conditions, washing, permanent waving, perspiration, and rubbing.

The oxidation dyes should also make it possible to cover white hair and, finally, be the least selective possible, that is to say, make it possible to obtain the smallest possible color differences along the same keratinous fiber, which may, indeed, be variously sensitized, i.e., damaged, between its end and its root.

The oxidation dyes (oxidation bases and couplers) used for the permanent dyeing of keratinous fibers are generally developed with the aid of oxidizing agents such as hydrogen peroxide. This type of developing certainly makes it possible to obtain intense colors, but it is not without consequence on the keratinous fibers, which unavoidably undergo decolorization and degradation of the fiber.

It has already been proposed, in particular, in European Patent Application EP-A-375 977, the disclosure of which is specifically incorporated herein by reference, to use certain ortho-diaminopyrazole derivatives, more specifically, 3,4- or 4,5-diaminopyrazole derivatives, such as, for example, 5 4,5-diaminopyrazole, for the oxidation dyeing of keratinous fibers in red shades. However, the dyeing process described in this patent application uses an oxidizing agent, such as hydrogen peroxide, such that an intense color cannot be obtained without the keratinous fiber being adversely affected and decolorized.

Indeed, it is known that some diaminopyrazoles, of a very specific structure, such as those described in German Patent Applications DE-A-4,234,886 and DE-A-4,234,887, the disclosures of which are specifically incorporated herein by reference, can be developed without any oxidizing agent other than atmospheric oxygen, thereby leading to colors which do not adversely affect the keratinous fibers.

However, in the specific case of the ortho-diaminopyrazoles which cannot be developed with atmospheric oxygen alone, as in the more general case of most other oxidation bases, such as, for example, ortho-diaminobenzene, it is unfortunately not possible to obtain a satisfactory color on the hair when a dyeing process is used which involves only atmospheric oxygen as the agent for developing the color on the hair.

Now, the inventor has discovered, completely unexpectedly and surprisingly, that manganese salts make it possible, without having to use an oxidizing agent other than atmospheric oxygen, to effectively develop the ortho-diaminopyrazoles which cannot normally be developed in air, i.e., atmospheric oxygen. This discovery forms the basis of the present invention.

In a preferred embodiment, there is no oxidizing agent present other than atmospheric oxygen. However, it is within the scope of the invention to include inconsequential amounts of oxidizing agents. As defined herein, inconsequential amounts include amounts of oxidizing agents that would be incapable of developing the ortho-diaminopyrazole/acid addition salt thereof in the presence of atmospheric oxygen unless an effective amount of manganese is included. In other words, the ortho-diaminopyrazole/acid addition salt is incapable of being effectively developed with atmospheric oxygen and inconsequential amounts of oxidizing agent alone, unless the effective amount of manganese salt is present. Accordingly, development of the composition of the invention in the presence of atmospheric oxygen and inconsequential amounts of oxidizing agent is considered as development without any oxidizing agent other than atmospheric oxygen. Although not preferred, it is also possible to use the composition of the present invention in the presence of atmospheric oxygen and consequential amounts of at least one oxidizing agent other than atmospheric oxygen.

A subject of the present invention is therefore a composition for dyeing keratinous fibers, and in particular human keratinous fibers such as the hair, which comprises, in a medium appropriate for dyeing:

at least one ortho-diaminopyrazole or one of its acid addition salts, which is incapable of being effectively developed with atmospheric oxygen alone, and at least one manganese salt, said at least one salt being present in an amount effective to develop said at least one ortho-diaminopyrazole or one of its acid addition salts in the presence of atmospheric oxygen.

In the compositions according to the invention, the ortho-diaminopyrazole and the manganese salt may be provided in the form of a mixture or may be packaged separately.

The dyeing composition in accordance with the invention does not need to be mixed at the time of use with a conventional oxidizing agent such as hydrogen peroxide; it leads, in addition, to rapid, intense and fast colors, without causing decolorization or damage of the keratinous fibers.

The term ortho-diaminopyrazole incapable of being effectively developed by atmospheric oxygen alone is understood to include any ortho-diaminopyrazole not leading to any satisfactory color of the keratinous fibers when it is developed with atmospheric oxygen alone, or as explained above, with atmospheric oxygen and an inconsequential amount of an oxidizing agent.

The ortho-diaminopyrazoles incapable of being effectively developed with atmospheric oxygen alone are thus preferably chosen from compounds of formula (I), and their acid addition salts:

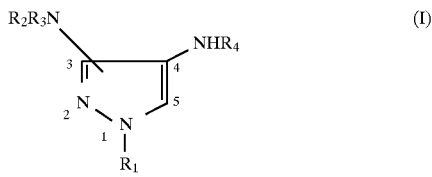

in which:
R$_1$, R$_2$ and R$_4$, which are identical or different, represent a hydrogen atom or a C$_1$–C$_4$ alkyl, C$_2$–C$_4$ monohydroxyalkyl, benzyl or phenyl radical, R$_3$ represents a hydrogen atom or a C$_1$–C$_4$ alkyl or C$_2$–C$_4$ monohydroxyalkyl radical, the amino group NR$_2$R$_3$ occupying either the 3-position or the 5-position of the compounds.

Among the compounds of formula (I) above, there may preferably be mentioned 4,5-diaminopyrazole, 4,5-diamino-1-methylpyrazole, 1-benzyl-4,5-diaminopyrazole, 3,4-diaminopyrazole, and their acid addition salts. 4,5-Diaminopyrazole and its acid addition salts are particularly preferred.

The manganese salts which may be used in the dyeing composition in accordance with the invention preferably do not have an inherent oxidizing activity and in these salts, the manganese preferably has an oxidation number equal to 2 or 3. It is of course possible to use one or more manganese salts.

The manganese salts are preferably chosen from manganese diacetate and its hydrates, such as, for example, manganese diacetate tetrahydrate, manganese dichloride and its hydrates, manganese sulphates, manganese carbonates, manganese dihydrogen carbonates, manganese acetylacetonate, manganese triacetate and its hydrates and manganese trichloride. Manganese diacetate tetrahydrate is particularly preferred.

According to the invention, the manganese salt or salts are preferably present at a concentration ranging from about 0.002 to 5% metal equivalent weight relative to the total weight of the dyeing composition. Still more preferably, this concentration ranges from about 0.005 to 0.5% metal equivalent weight relative to the total weight of the dyeing composition.

The ortho-diaminopyrazoles in accordance with the invention or their acid addition salts preferably represent from about 0.0005 to 12% by weight of the total weight of the dyeing composition, and still more preferably represent from about 0.005 to 6% by weight of this weight.

The appropriate medium for dyeing (or carrier) generally comprises water or a mixture of water and at least one organic solvent for solubilizing the components which may be insufficiently soluble in water. As organic solvent, there may preferably be mentioned, for example, the C$_1$–C$_4$ lower alkanols, such as ethanol and isopropanol; glycerol; glycols or glycol ethers, such as 2-butoxyethanol, propylene glycol, propylene glycol monomethyl ether, diethylene glycol monoethyl ether and monomethyl ether, as well as aromatic alcohols, such as benzyl alcohol and phenoxyethanol, analogous products and mixtures thereof.

The solvents may be present in proportions preferably ranging from about 1 to 40% by weight relative to the total weight of the dyeing composition, and still more preferably ranging from 5 to 30% by weight.

The pH of the dyeing composition in accordance with the invention is preferably greater than or equal to 7, and more preferably ranges from about 9 to 12. The pH may be adjusted to the desired value by means of alkalinizing and, where appropriate, acidifying agents normally used in dyeing keratinous fibers.

Among the alkalinizing agents, there may be mentioned, by way of example, ammonium hydroxide, alkali metal carbonates, alkanolamines such as mono-, di- and triethanolamines, as well as derivatives thereof, sodium or potassium hydroxides and compounds of the formula (II):

in which W is a propylene residue optionally substituted with a hydroxyl group or a C$_1$–C$_4$ alkyl radical; R$_6$, R$_7$, R$_8$ and R$_9$, which are identical or different, represent a hydrogen atom or a C$_1$–C$_4$ alkyl or C$_1$–C$_4$ hydroxyalkyl radical.

Among the acidifying agents, there may be mentioned, by way of example, inorganic or organic acids such as hydrochloric acid, orthophosphoric acid, sulphuric acid, carboxylic acids, such as acetic acid, tartaric acid, citric acid, and lactic acid, and sulphonic acids.

The dyeing composition in accordance with the invention may also preferably contain at least one coupler and/or at least one direct dye to modify the shades or to enrich their shimmer.

The couplers which can be used in accordance with the invention may preferably be chosen from the couplers conventionally used in oxidation dyeing and among which there may more preferably be mentioned meta-phenylenediamines, meta-aminophenols, meta-diphenols and heterocyclic couplers, such as, for example, indole derivatives, indoline derivatives, and their addition salts with an acid.

These couplers may preferably be chosen from 2-methyl-5-amino-phenol, 5-N-(β-hydroxyethyl)amino-2-methylphenol, 3-aminophenol, 1,3-dihydroxybenzene, 1,3-dihydroxy-2-methylbenzene, 4-chloro-1,3-dihidroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, and their acid addition salts.

When they are present, these couplers preferably represent from about 0.0001 to 10% by weight of the total weight of the dyeing composition, and still more preferably from about 0.005 to 5% by weight of this weight.

The acid addition salts of the ortho-diaminopyrazole(s) in accordance with the invention and/or of the couplers which can be used in accordance with the invention are preferably chosen from hydrochlorides, hydrobromides, sulphates, tartrates, lactates and acetates.

The dyeing composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic anionic polymers or mixtures thereof, inorganic or organic thickening agents, antioxidants, penetrating agents, sequestering agents, perfumes, buffers, dispersing agents, conditioning agents such as for example silicones, film-forming agents, preservatives and opacifying agents.

Of course, persons skilled in the art will take care to choose the possible additional compounds mentioned above, such that the advantageous properties intrinsically attached to the dyeing composition in accordance with the invention are not, or are not substantially, altered by the addition(s) envisaged.

The dyeing composition in accordance with the invention may be provided in various forms, such as in the form of liquids, creams, gels, shampoos or any other form appropriate for dyeing keratinous fibers, and especially human hair.

The dyeing compositions are preferably prepared under an inert gas such as argon and packaged out of contact with air so as to avoid any premature oxidation of the ortho-diaminopyrazoles in accordance with the invention.

Another subject of the invention is a multicompartment device or multicompartment dyeing kit or any other multi-compartment packaging system, containing at least two compartments, in which a first compartment comprises a composition A containing, in a medium appropriate for dyeing, at least one ortho-diaminopyrazole or acid addition salt thereof incapable of being effectively developed with atmospheric oxygen alone, and a second compartment comprises a composition B containing, in a medium appropriate for dyeing, at least one manganese salt, as defined above. These devices or kits may be equipped with means which allow the desired mixture to be delivered to the hair, such as the devices described in L'Oréal's French Patent No. FR 2,586,913, the disclosure of which is incorporated herein by reference.

A subject of the invention is also a process for dyeing keratinous fibers, and in particular human keratinous fibers such as hair, using the dyeing composition as defined above.

According to this process, at least one dyeing composition as defined above is applied to the fibers for an exposure time sufficient to develop the desired color, the color being developed in the air and preferably without any oxidizing agent other than atmospheric oxygen.

According to a preferred embodiment of the dyeing process in accordance with the invention, the dyeing composition is applied to the keratinous fibers for an exposure time preferably varying from between 30 seconds to 40 minutes, after which the fibers are rinsed, optionally washed with shampoo and then dried.

When the dyeing composition in accordance with the invention is present in the form of a multicompartment dyeing kit, the process in accordance with the invention comprises, in this case, a preliminary step consisting in mixing, at the time of use, the components A and B defined above, the mixture obtained then being applied to the keratinous fibers according to the conditions defined above.

The examples which follow are intended to illustrate the invention without thereby limiting the scope thereof.

EXAMPLES

Comparative Example 1

The following dyeing compositions 1A, 1B, 1C and 1D were prepared:

| Composition 1A not forming part of the invention: | |
| --- | --- |
| 4,5-diaminopyrazole dihydrochloride | 0.382 g |
| 2,4-diamino-1-(β-hydroxyethyloxy)benzene dihydrochloride | 0.482 g |
| ethyl alcohol | 10 g |
| monoethanolamine | 5 g |
| demineralized water qs | 100 g |
| pH = 10.5 | |

| Composition 1B forming part of the invention: | |
| --- | --- |
| 4,5-diaminopyrazole dihydrochloride | 0.382 g |
| 2,4-diamino-1-(β-hydroxyethyloxy)benzene dihydrochloride | 0.482 g |
| manganese diacetate tetrahydrate | 0.1 g |
| ethyl alcohol | 10 g |
| monoethanolamine | 5 g |
| demineralized water qs | 100 g |
| pH = 10.5 | |

| Composition 1C not forming part of the invention: | |
| --- | --- |
| ortho-diaminobenzene | 0.218 g |
| 2,4-diamino-1-(β-hydroxyethyloxy)benzene dihydrochloride | 0.482 g |
| ethyl alcohol | 10 g |
| monoethanolamine | 5 g |
| demineralized water qs | 100 g |
| pH = 10.5 | |

| Composition 1D not forming part of the invention: | |
| --- | --- |
| ortho-diaminobenzene | 0.218 g |
| 2,4-diamino-1-(β-hydroxyethyloxy)benzene dihydrochloride | 0.482 g |
| manganese diacetate tetrahydrate | 0.1 g |
| ethyl alcohol | 10 g |
| monoethanolamine | 5 g |
| demineralized water qs | 100 g |
| pH = 10.5 | |

The compositions 1A, 1B, 1C and 1D were prepared under argon.

Each composition 1A, 1B, 1C and 1D was applied to locks of dry natural grey hair which was 90% white for 30 minutes. The locks of hair were then rinsed, washed with a standard shampoo and then dried.

The lock having been subjected to the application of composition 1A, not forming part of the invention (because it contains no manganese salt), had no color whereas the lock which was subjected to application of composition 1B in accordance with the invention (because it contains a manganese salt) was colored in an intense dark purple shade.

Moreover, the locks which were subjected to the application of compositions 1C or 1D, not forming part of the invention because they contain ortho-diaminobenzene and not an ortho-diaminopyrazol in accordance with the invention, resulted in no color, in the presence or absence of manganese salt.

EXAMPLE 2

A shampoo, in accordance with the invention, of the following composition was prepared under argon:

| | |
| --- | --- |
| 4,5-diaminopyrazole dihydrochloride | 0.382 g |
| 2,4-diamino-1-(β-hydroxyethyloxy)benzene dihydrochloride | 0.482 g |
| manganese diacetate tetrahydrate | 0.1 g |
| sodium lauryl sulphate | 1.5 g |
| monoethanolamine | 3 g |
| demineralized water qs | 100 g |
| pH = 10 | |

This shampoo was applied and emulsified for 2 minutes on wet natural grey hair which was 90% white. After rinsing and drying, the hair had a pink color.

EXAMPLE 3

The following dyeing composition in accordance with the invention was prepared under argon:

| | |
|---|---|
| 4,5-diaminopyrazole dihydrochloride | 0.382 g |
| 4-hydroxyindole | 0.266 g |
| manganese diacetate tetrahydrate | 0.1 g |
| ethyl alcohol | 10 g |
| monoethanolamine | 5 g |
| demineralized water qs | 100 g |
| pH = 10.5 | |

This composition was applied to permanently waved grey hair which was 90% white for 30 minutes. The hair was then rinsed, washed with shampoo and then dried.

The locks of hair were dyed in an intense violet shade.

What is claimed is:

1. A composition for dyeing keratinous fibers, which comprises, in a medium appropriate for dyeing:
   at least one ortho-diaminopyrazole or one of its acid addition salts which is incapable of being effectively developed with atmospheric oxygen alone,
   at least one coupler or one direct dye, and
   at least one manganese salt, said at least one manganese salt being present in an amount effective to develop said at least one ortho-diaminopyrazole or one of its acid addition salts in the presence of atmospheric oxygen,
   wherein said at least one ortho-diaminopyrazole, said at least one coupler or direct dye and said at least one manganese salt are each present in an amount effective to dye said keratin fibers.

2. A composition according to claim 1, wherein said keratinous fibers are hair.

3. A composition according to claim 1, wherein said at least one ortho-diaminopyrazole is selected from compounds of formula (I), and their acid addition salts:

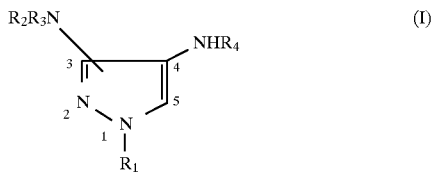

in which:
   $R_1$, $R_2$ and $R_4$, which are identical or different, represent a hydrogen atom or a $C_1$–$C_4$ alkyl, $C_2$–$C_4$ monohydroxyalkyl, benzyl or phenyl radical,
   $R_3$ represents a hydrogen atom or a $C_1$–$C_4$ alkyl or $C_2$–$C_4$ monohydroxyalkyl radical, wherein the amino group $NR_2R_3$ occupies the 3-position or the 5-position of said compounds.

4. A composition according to claim 3, wherein said at least one ortho-diaminopyrazole is selected from 4,5-diaminopyrazole, 4,5-diamino-1-methylpyrazole, 1-benzyl-4,5-diaminopyrazole, 3,4-diaminopyrazole, and their acid addition salts.

5. A composition according to claim 4, wherein said at least one diaminopyrazole is selected from 4,5-diaminopyrazole or one of its acid addition salts.

6. A composition according to claim 1, wherein the manganese of said at least one manganese salt has an oxidation number equal to 2 or 3.

7. A composition according claim 1, wherein said at least one manganese salt is selected from manganese diacetate tetrahydrate, manganese dichloride and its hydrates, manganese sulphates, manganese carbonates, manganese dihydrogen carbonates, manganese acetylacetonate, manganese triacetate and its hydrates and manganese trichloride.

8. A composition according to claim 7, wherein said at least one manganese salt is manganese diacetate tetrahydrate.

9. A composition according to claim 1, wherein said at least one manganese salt is present at a concentration ranging from 0.002 to 5% of metal equivalent weight relative to the total weight of the dyeing composition.

10. A composition according to claim 9, wherein said at least one manganese salt is present at a concentration ranging from 0.005 to 0.5% of metal equivalent weight relative to the total weight of the dyeing composition.

11. A composition according to claim 1, wherein said at least one ortho-diaminopyrazole or one of its acid addition salts represents from 0.0005 to 12% by weight of the total weight of the dyeing composition.

12. A composition according to claim 11, wherein said at least one ortho-diaminopyrazole or one of its acid addition salts represents from 0.005 to 6% by weight of the total weight of the dyeing composition.

13. A composition according to claim 1, wherein said medium appropriate for dyeing comprises water or a mixture of water and at least one organic solvent selected from $C_1$–$C_4$ lower alkanols, glycerol, glycols and glycol ethers and aromatic alcohols.

14. A composition according to claim 1, wherein said medium appropriate for dying represents from about 1 to 40% by weight relative to the total weight of the dyeing composition.

15. A composition according to claim 14, wherein said medium appropriate for dying represents from about 5 to 30% by weight relative to the total weight of the dyeing composition.

16. A composition according to claim 1, wherein said composition has a pH greater than or equal to 7.

17. A composition according to claim 16, wherein said composition has a pH ranging from 9 to 12.

18. A composition according to claim 1, wherein said at least one coupler is selected from meta-phenylenediamines, meta-aminophenols, meta-diphenols, heterocyclic couplers, and their acid addition salts.

19. A composition according to claim 18, wherein said heterocyclic couplers are selected from indole derivatives and indoline derivatives.

20. A composition according to claim 18, wherein said at least one coupler is selected from:
2-methyl-5-amino-phenol,
5-N-(β-hydroxyethyl)amino-2-methylphenol,
3-aminophenol,
1,3-dihydroxybenzene,
1,3-dihydroxy-2-methylbenzene,
4-chloro-1,3-di-hydroxybenzene,
2,4-diamino-1-(β-hydroxyethyloxy)-benzene,
2-amino-4-(β-hydroxyethylamino)-1-methoxy-benzene,
1,3-diaminobenzene,
1,3-bis(2,4-diamino-phenoxy)propane,
sesamol,
α-naphthol,
6-hydroxyindole,
4-hydroxyindole,
4-hydroxy-N-methylindole,
6-hydroxy-indoline, and their acid addition salts.

21. A composition according to claim 1, wherein said at least one coupler represents from about 0.001 to 10% by weight of the total weight of the dyeing composition.

22. A composition according to claim 21, wherein said at least one coupler represents from about 0.005 to 5% by weight of the total weight of the dyeing composition.

23. A composition according claim 1, wherein said acid addition salts of said at least one ortho-diaminopyrazole are selected from hydrochlorides, hydrobromides, sulphates, tartrates, lactates and acetates.

24. A composition according to claim 18, wherein said acid addition salts of said at least one coupler are selected from hydrochlorides, hydrobromides, sulphates, tartrates, lactates and acetates.

25. A process for dyeing keratinous fibers, which comprises applying a dyeing composition according to claim 1 to said keratinous fibers for an exposure time sufficient to develop a desired color, wherein said color is developed in the air without any oxidizing agent other than atmospheric oxygen.

26. A process according to claim 25, wherein said dyeing composition is applied to said keratinous fibers for an exposure time ranging from 30 seconds to 40 minutes.

27. A multicompartment device or multicompartment dyeing kit, comprising at least a first and a second compartment, wherein said first compartment comprises a composition A containing, in a medium appropriate for dyeing, at least one ortho-diaminopyrazole or one of its acid addition salts incapable of being effectively developed with atmospheric oxygen alone and at least one coupler or one direct dye, and wherein said second compartment comprises a composition B containing, in a medium appropriate for dyeing, at least one manganese salt having an oxidation number equal to 2 or 3, wherein said at least one ortho-diaminopyrazole, said at least one coupler or direct dye and said at least one manganese salt are each present in an amount effective to dye said keratin fibers.

28. A process for dyeing keratinous fibers, which comprises:

obtaining a dyeing composition from a multicompartment dyeing device comprising at least a first and a second compartment, wherein said first compartment comprises a composition A containing, in a medium appropriate for dyeing, at least one ortho-diaminopyrazole or one of its acid addition salts incapable of being effectively developed with atmospheric oxygen alone and at least one coupler or one direct dye, and wherein said second compartment comprises a composition B containing, in a medium appropriate for dyeing, at least one manganese salt having an oxidation number equal to 2 or 3, mixing, at the time of application, said composition A and said composition B to form a mixture, and applying said mixture to said keratinous fibers for an exposure time sufficient to develop a desired color, wherein said color is developed in the air without any oxidizing agent other than atmospheric oxygen.

29. A process according to claim 28, wherein said dyeing composition is applied to said keratinous fibers for an exposure time ranging from 30 seconds to 40 minutes.

30. A process for dyeing keratinous fibers, which comprises applying a dyeing composition according to claim 1 to said keratinous fibers for an exposure time sufficient to develop the desired color, wherein said color is developed in the presence of atmospheric oxygen and of at least one oxidizing agent other than said atmospheric oxygen.

* * * * *

UNITED STATES PATENT AND TRADEMARK OFFICE
CERTIFICATE OF CORRECTION

PATENT NO.   : 5,769,902
DATED        : June 23, 1998
INVENTOR(S)  : Henri Samain It is certified that error appears in the above-identified patent and that said Letters Patent is hereby corrected as shown below:

Title page,
Item [54], Title, change "COMPSITIONS" to -- COMPOSITIONS --; and change "DIAMINOPYRAZOLES" to -- DIAMINOPYRAZOLE --.

Column 10,
Line 27, delete "of" (second occurrence).

Signed and Sealed this

First Day of April, 2003

JAMES E. ROGAN
*Director of the United States Patent and Trademark Office*